(12) United States Patent
Quick et al.

(10) Patent No.: US 8,915,864 B2
(45) Date of Patent: Dec. 23, 2014

(54) BIOPSY DEVICE WITH FLUID DELIVERY TO TISSUE SPECIMENS

(71) Applicant: SenoRx, Inc., Tempe, AZ (US)

(72) Inventors: Richard L. Quick, Mission Viejo, CA (US); Martin V. Shabaz, Lake Forest, CA (US); Frank R. Louw, Carlsbad, CA (US); Paul Lubock, Monarch Beach, CA (US); Jason H. Safabash, Aliso Viejo, CA (US)

(73) Assignee: SenoRx, Inc., Tempe, AZ (US)

( * ) Notice: Subject to any disclaimer, the term of this patent is extended or adjusted under 35 U.S.C. 154(b) by 0 days.

(21) Appl. No.: 13/683,890

(22) Filed: Nov. 21, 2012

(65) Prior Publication Data

US 2013/0079664 A1    Mar. 28, 2013

Related U.S. Application Data

(60) Continuation of application No. 11/980,298, filed on Oct. 30, 2007, now Pat. No. 8,317,725, which is a division of application No. 11/498,504, filed on Aug. 3, 2006, now Pat. No. 7,572,236, which is a continuation-in-part of application No. 11/197,827, filed on Aug. 5, 2005, now abandoned.

(51) Int. Cl.
  *A61B 10/00* (2006.01)
  *A61B 10/02* (2006.01)
  *A61M 1/00* (2006.01)

(52) U.S. Cl.
  CPC ..... *A61B 10/0266* (2013.01); *A61B 2010/0208* (2013.01); *A61B 10/0275* (2013.01); *A61B 10/0283* (2013.01); *A61M 1/0056* (2013.01); *A61B 2217/005* (2013.01)
  USPC .......................................... 600/566; 600/568

(58) Field of Classification Search
  CPC ................... A61B 2217/005; A61M 1/0056
  USPC ................................................ 600/566, 568
  See application file for complete search history.

(56) References Cited

U.S. PATENT DOCUMENTS

| 2,032,860 | A | 3/1936 | Wappler et al. |
| 2,192,270 | A | 3/1940 | McGowan |

(Continued)

FOREIGN PATENT DOCUMENTS

| DE | 19528440 A1 | 2/1997 |
| EP | 0146699 A1 | 7/1985 |

(Continued)

OTHER PUBLICATIONS

Armstrong, J.S. et al., "Differential marking of excision planes in screened breast lesions by organically coloured gelantins", Journal of Clinical Pathology, (Jul. 1990), 43(7) 604-7, XP000971447 abstract; tables 1 and 2.

(Continued)

*Primary Examiner* — Max Hindenburg
*Assistant Examiner* — Renee Danega

(57) ABSTRACT

The invention is directed to a system and method for separating and collecting one or more tissue specimens from a target site within a patient and flushing the specimen to remove blood, debris and the like before the specimen is removed from the biopsy device. The flow of flushing fluid to the tissue collector is preferably controlled to coincide with delivery of one or more specimens to the collecting tray or basket of the device or after the receipt of the specimen within the tissue collector to ensure that the fluid is applied to a fresh specimen. The tissue tray or basket within the tissue collector has an open or foraminous portion to facilitate removal of fluid, such as the applied fluid and blood, and other debris from the tissue specimens on the tray. Vacuum is provided within the tissue collector, preferably under the tray to remove fluid and debris from the collector interior.

19 Claims, 14 Drawing Sheets

(56) References Cited

U.S. PATENT DOCUMENTS

| | | |
|---|---|---|
| 3,341,417 A | 9/1967 | Sinaiko |
| 3,805,791 A | 4/1974 | Seuberth et al. |
| 3,815,604 A | 6/1974 | O'Malley et al. |
| 3,818,894 A | 6/1974 | Wichterle et al. |
| 3,823,212 A | 7/1974 | Chvapil |
| 3,844,272 A | 10/1974 | Banko |
| 3,847,153 A | 11/1974 | Weissman |
| 3,910,279 A | 10/1975 | Okada et al. |
| 3,945,375 A | 3/1976 | Banko |
| 3,955,578 A | 5/1976 | Chamness et al. |
| 4,007,732 A | 2/1977 | Kvavle et al. |
| 4,074,562 A | 2/1978 | North, Jr. |
| 4,172,449 A | 10/1979 | LeRoy et al. |
| 4,197,846 A | 4/1980 | Bucalo |
| 4,202,338 A | 5/1980 | Bitrolf |
| 4,243,048 A | 1/1981 | Griffin |
| 4,250,892 A * | 2/1981 | Dolhay et al. .......... 600/571 |
| 4,276,885 A | 7/1981 | Tickner et al. |
| 4,294,241 A | 10/1981 | Miyata |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,418,692 A | 12/1983 | Guay |
| 4,503,855 A | 3/1985 | Maslanka |
| 4,545,367 A | 10/1985 | Tucci |
| 4,565,200 A | 1/1986 | Cosman |
| 4,576,162 A | 3/1986 | McCorkle |
| 4,638,802 A | 1/1987 | Okada |
| 4,643,187 A | 2/1987 | Okada |
| 4,647,480 A | 3/1987 | Ahmed |
| 4,682,606 A | 7/1987 | DeCaprio |
| 4,693,237 A | 9/1987 | Hoffman et al. |
| 4,718,419 A | 1/1988 | Okada |
| 4,724,836 A | 2/1988 | Okada |
| 4,729,764 A | 3/1988 | Gualtier |
| 4,813,062 A | 3/1989 | Gilpatrick |
| 4,847,049 A | 7/1989 | Yamamoto |
| 4,863,470 A | 9/1989 | Carter |
| 4,909,250 A | 3/1990 | Smith |
| 4,926,858 A | 5/1990 | Gifford, III et al. |
| 5,007,908 A | 4/1991 | Rydell |
| 5,024,617 A | 6/1991 | Karpiel |
| 5,035,696 A | 7/1991 | Rydell |
| 5,041,124 A | 8/1991 | Kensey |
| 5,047,027 A | 9/1991 | Rydell |
| 5,059,204 A | 10/1991 | Lawson et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| RE33,925 E | 5/1992 | Bales et al. |
| 5,111,828 A | 5/1992 | Kornberg et al. |
| 5,133,359 A | 7/1992 | Kedem |
| 5,133,360 A | 7/1992 | Spears |
| RE34,056 E | 9/1992 | Lindgren et al. |
| 5,147,307 A | 9/1992 | Gluck |
| 5,158,561 A | 10/1992 | Rydell et al. |
| 5,163,938 A | 11/1992 | Kambara et al. |
| 5,196,007 A | 3/1993 | Ellman et al. |
| 5,201,732 A | 4/1993 | Parins et al. |
| 5,201,741 A | 4/1993 | Dulebohm |
| 5,207,686 A | 5/1993 | Dolgin |
| 5,217,458 A | 6/1993 | Parins |
| 5,224,488 A | 7/1993 | Neuffer |
| 5,236,410 A | 8/1993 | Granov et al. |
| 5,258,006 A | 11/1993 | Rydell et al. |
| 5,281,218 A | 1/1994 | Imran |
| 5,281,408 A | 1/1994 | Unger |
| 5,282,781 A | 2/1994 | Liprie |
| 5,312,400 A | 5/1994 | Bales et al. |
| 5,318,564 A | 6/1994 | Eggers |
| 5,320,613 A | 6/1994 | Houge et al. |
| 5,323,768 A | 6/1994 | Saito et al. |
| 5,324,288 A | 6/1994 | Billings et al. |
| 5,330,471 A | 7/1994 | Eggers |
| 5,334,381 A | 8/1994 | Unger |
| 5,335,671 A | 8/1994 | Clement |
| 5,344,381 A | 9/1994 | Cabrera y Lopez Caram |
| 5,344,420 A | 9/1994 | Hilal et al. |
| 5,368,030 A | 11/1994 | Zinreich et al. |
| 5,374,188 A | 12/1994 | Frank et al. |
| 5,376,094 A | 12/1994 | Kline |
| 5,380,321 A | 1/1995 | Yoon |
| 5,395,312 A | 3/1995 | Desai |
| 5,395,319 A | 3/1995 | Hirsch et al. |
| 5,401,272 A | 3/1995 | Perkins |
| 5,415,656 A | 5/1995 | Tihon et al. |
| 5,417,687 A | 5/1995 | Nardella et al. |
| 5,417,697 A | 5/1995 | Wilk |
| 5,422,730 A | 6/1995 | Barlow et al. |
| 5,423,809 A | 6/1995 | Klicek |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,498 A | 8/1995 | Perkins |
| 5,441,503 A | 8/1995 | Considine et al. |
| 5,462,553 A | 10/1995 | Dolgin |
| 5,470,308 A | 11/1995 | Edwards et al. |
| 5,477,862 A | 12/1995 | Haaga |
| 5,484,436 A | 1/1996 | Eggers et al. |
| 5,487,385 A | 1/1996 | Avitall |
| 5,488,958 A | 2/1996 | Topel et al. |
| 5,494,030 A | 2/1996 | Swartz et al. |
| 5,501,654 A | 3/1996 | Failla et al. |
| 5,507,743 A | 4/1996 | Edwards et al. |
| 5,526,822 A | 6/1996 | Burbank et al. |
| 5,527,331 A | 6/1996 | Kresch et al. |
| 5,536,267 A | 7/1996 | Edwards et al. |
| 5,538,010 A | 7/1996 | Darr et al. |
| 5,542,948 A | 8/1996 | Weaver et al. |
| 5,549,560 A | 8/1996 | Van de Wijdeven |
| 5,578,030 A | 11/1996 | Levin |
| 5,595,185 A | 1/1997 | Erlich |
| 5,599,347 A | 2/1997 | Hart et al. |
| 5,607,389 A | 3/1997 | Edwards et al. |
| 5,611,803 A | 3/1997 | Heaven et al. |
| 5,636,255 A | 6/1997 | Ellis |
| 5,643,282 A | 7/1997 | Kieturakis |
| 5,646,146 A | 7/1997 | Faarup et al. |
| 5,649,547 A | 7/1997 | Ritchart et al. |
| 5,653,718 A | 8/1997 | Yoon |
| 5,665,085 A | 9/1997 | Nardella |
| 5,672,174 A | 9/1997 | Gough et al. |
| 5,674,184 A | 10/1997 | Hassler, Jr. |
| 5,676,663 A | 10/1997 | Kim |
| 5,676,925 A | 10/1997 | Klaveness et al. |
| 5,683,384 A | 11/1997 | Gough et al. |
| 5,687,739 A | 11/1997 | McPherson et al. |
| 5,688,490 A | 11/1997 | Tournier et al. |
| 5,715,825 A | 2/1998 | Crowley |
| 5,720,763 A | 2/1998 | Tovey |
| 5,741,225 A | 4/1998 | Lax et al. |
| 5,749,626 A | 5/1998 | Yoshida |
| 5,766,134 A | 6/1998 | Lisak et al. |
| 5,766,169 A | 6/1998 | Fritzsch et al. |
| 5,769,086 A | 6/1998 | Ritchart et al. |
| 5,772,660 A | 6/1998 | Young et al. |
| 5,775,333 A | 7/1998 | Burbank et al. |
| 5,782,764 A | 7/1998 | Werne |
| 5,782,775 A | 7/1998 | Milliman et al. |
| 5,782,827 A | 7/1998 | Gough et al. |
| 5,786,207 A | 7/1998 | Katz et al. |
| 5,794,626 A | 8/1998 | Kieturakis |
| 5,797,907 A | 8/1998 | Clement |
| 5,800,378 A | 9/1998 | Edwards et al. |
| 5,810,806 A | 9/1998 | Ritchart et al. |
| 5,814,044 A | 9/1998 | Hooven |
| 5,846,513 A | 12/1998 | Carroll et al. |
| 5,848,978 A | 12/1998 | Cecchi |
| 5,853,366 A | 12/1998 | Dowlatshahi |
| 5,857,981 A | 1/1999 | Bucalo et al. |

(56) References Cited

U.S. PATENT DOCUMENTS

| | | |
|---|---|---|
| 5,857,982 A | 1/1999 | Milliman et al. |
| 5,876,340 A | 3/1999 | Tu et al. |
| 5,882,316 A | 3/1999 | Chu et al. |
| 5,902,272 A | 5/1999 | Eggers et al. |
| 5,913,857 A | 6/1999 | Ritchart et al. |
| 5,925,044 A | 7/1999 | Hoffman et al. |
| 5,928,164 A | 7/1999 | Burbank et al. |
| 5,938,587 A | 8/1999 | Taylor et al. |
| 5,941,893 A | 8/1999 | Saadat |
| 5,947,964 A | 9/1999 | Eggers et al. |
| 5,954,670 A | 9/1999 | Baker |
| 5,964,716 A | 10/1999 | Gregoire et al. |
| 5,972,002 A | 10/1999 | Bark et al. |
| 5,980,469 A | 11/1999 | Burbank et al. |
| 5,984,919 A | 11/1999 | Hilal et al. |
| 5,997,560 A | 12/1999 | Miller |
| 6,004,269 A | 12/1999 | Crowley et al. |
| 6,036,681 A | 3/2000 | Hooven |
| 6,050,955 A | 4/2000 | Bryan et al. |
| 6,050,992 A | 4/2000 | Nichols |
| 6,056,700 A | 5/2000 | Burney et al. |
| 6,059,782 A | 5/2000 | Novak et al. |
| 6,063,082 A | 5/2000 | DeVore et al. |
| 6,071,280 A | 6/2000 | Edwards et al. |
| 6,120,462 A | 9/2000 | Hibner et al. |
| 6,142,955 A | 11/2000 | Farascioni et al. |
| 6,161,034 A | 12/2000 | Burbank et al. |
| 6,203,524 B1 | 3/2001 | Burney et al. |
| 6,220,248 B1 | 4/2001 | Voegele et al. |
| 6,234,177 B1 | 5/2001 | Barsch |
| 6,254,601 B1 | 7/2001 | Burbank et al. |
| 6,261,241 B1 | 7/2001 | Burbank et al. |
| 6,277,083 B1 | 8/2001 | Eggers et al. |
| 6,312,429 B1 | 11/2001 | Burbank et al. |
| 6,331,166 B1 | 12/2001 | Burbank et al. |
| 6,344,026 B1 | 2/2002 | Burbank et al. |
| 6,350,244 B1 | 2/2002 | Fisher |
| 6,454,727 B1 | 9/2002 | Burbank et al. |
| 6,485,436 B1 | 11/2002 | Truckai et al. |
| 6,494,881 B1 | 12/2002 | Bales et al. |
| 6,514,215 B1 | 2/2003 | Ouchi |
| 6,514,248 B1 | 2/2003 | Eggers et al. |
| 6,540,695 B1 | 4/2003 | Burbank et al. |
| 6,679,851 B2 | 1/2004 | Burbank et al. |
| 6,689,145 B2 | 2/2004 | Lee et al. |
| 6,712,775 B2 | 3/2004 | Burbank et al. |
| 6,758,824 B1 | 7/2004 | Miller et al. |
| 7,189,206 B2 | 3/2007 | Quick et al. |
| 7,226,424 B2 | 6/2007 | Ritchart et al. |
| 7,572,236 B2 | 8/2009 | Quick et al. |
| 7,621,917 B2 * | 11/2009 | Geneve et al. ............ 606/86 R |
| 7,981,051 B2 | 7/2011 | Quick et al. |
| 8,088,079 B2 | 1/2012 | Kaye et al. |
| 8,109,886 B2 | 2/2012 | Miller et al. |
| 2001/0001811 A1 | 5/2001 | Burney et al. |
| 2001/0002250 A1 | 5/2001 | Burbank et al. |
| 2002/0016555 A1 | 2/2002 | Ritchart et al. |
| 2002/0193705 A1 | 12/2002 | Burbank et al. |
| 2003/0004407 A1 | 1/2003 | Carroll et al. |
| 2003/0069543 A1 | 4/2003 | Carpenter et al. |
| 2003/0125639 A1 | 7/2003 | Fisher et al. |
| 2003/0130594 A1 | 7/2003 | Hynes et al. |
| 2003/0199787 A1 | 10/2003 | Schwindt |
| 2004/0019299 A1 | 1/2004 | Ritchart et al. |
| 2004/0191897 A1 * | 9/2004 | Muschler ............ 435/325 |
| 2005/0065453 A1 | 3/2005 | Shabaz et al. |

FOREIGN PATENT DOCUMENTS

| | | |
|---|---|---|
| EP | 0255123 A2 | 2/1988 |
| EP | 0292936 A2 | 11/1988 |
| EP | 0472368 A2 | 2/1992 |
| EP | 0481685 A1 | 4/1992 |
| EP | 0509670 A2 | 10/1992 |
| EP | 0601709 A2 | 6/1994 |
| EP | 0667126 A1 | 8/1995 |
| EP | 0769281 A2 | 10/1995 |
| EP | 0858774 A2 | 1/1997 |
| EP | 0966925 A1 | 6/1998 |
| EP | 0970658 A1 | 6/1998 |
| EP | 1698283 A1 | 3/2006 |
| GB | 2311468 A | 2/1997 |
| WO | 9313718 A1 | 7/1993 |
| WO | 9314712 A1 | 8/1993 |
| WO | 9502370 A2 | 1/1995 |
| WO | 9502371 A2 | 1/1995 |
| WO | 9608208 A1 | 3/1996 |
| WO | 9806346 A1 | 2/1998 |
| WO | 9808441 A1 | 3/1998 |
| WO | 9930764 A1 | 6/1999 |
| WO | 9944506 A1 | 9/1999 |
| WO | 0012009 A2 | 3/2000 |
| WO | 0016697 A2 | 3/2000 |
| WO | 0030531 A1 | 6/2000 |
| WO | 0205717 A1 | 1/2002 |
| WO | 0222023 A1 | 3/2002 |
| WO | 02062228 A1 | 8/2002 |
| WO | 02062232 A1 | 8/2002 |
| WO | 2004043531 A2 | 5/2004 |
| WO | 2004052212 A1 | 6/2004 |
| WO | 2004075719 A2 | 9/2004 |
| WO | 2005063126 A2 | 7/2005 |
| WO | 2006049911 A1 | 5/2006 |

OTHER PUBLICATIONS

Burbank, F., M.D., Stereotactic Breast Biopsy: Its History, Its Present, and Its Future, The American Surgeon, Feb. 1996, vol. 62, pp. 128-150.

Fucci, V. et al., "Large Bowel Transit Times Using Radiopaque Markers in Normal Cats", J. Of Am. Animal Hospital Assn., Nov.-Dec. 1995 vol. 31 (6) 473-477.

Lorenzen, T. et al., The Loop Electrode: a New Device for US-guided Interstitial Tissue Ablation Using Radio frequency Electrosurgery—An Animal Study, 1996 Blackwell Science Ltd. Min Incas Ther & Allied Technol, pp. 5.511-5.516.

Micklos, Timothy J., Percutaneous Biopsy Techniques, Manual of Oncologic Therapeutics (1989/1990) pp. 39-42.

Schindlebeck, N. E., et al., "Measurement of Colon Transit Time", J. of Gastroenterology, No. 28, pp. 399-404, 1990.

Whitman, et al., Coaxial Core Needle Biopsy Under Mammographic Guidance: Indications and Applications, AJR:171, Jul. 1998, pp. 67-70.

* cited by examiner

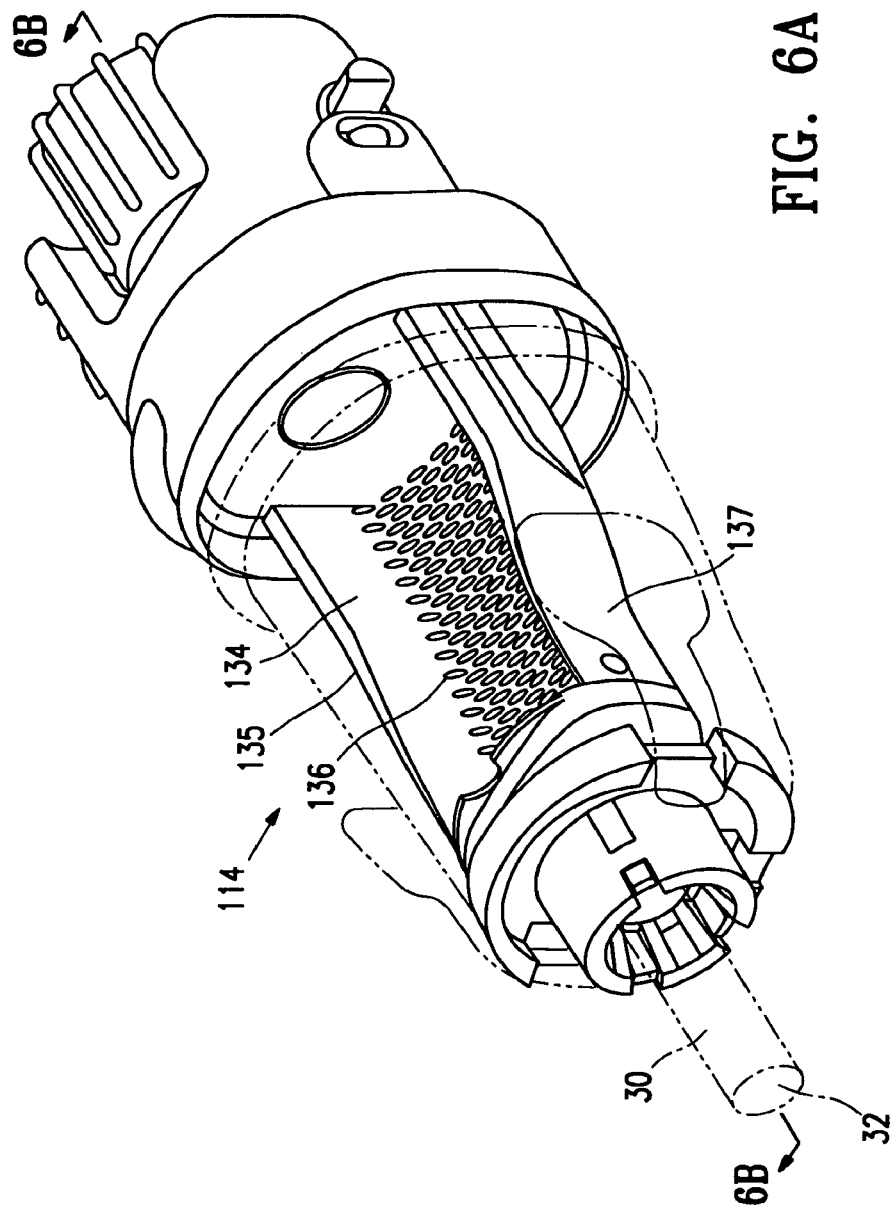

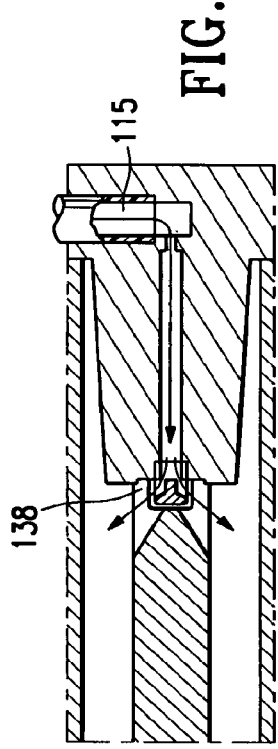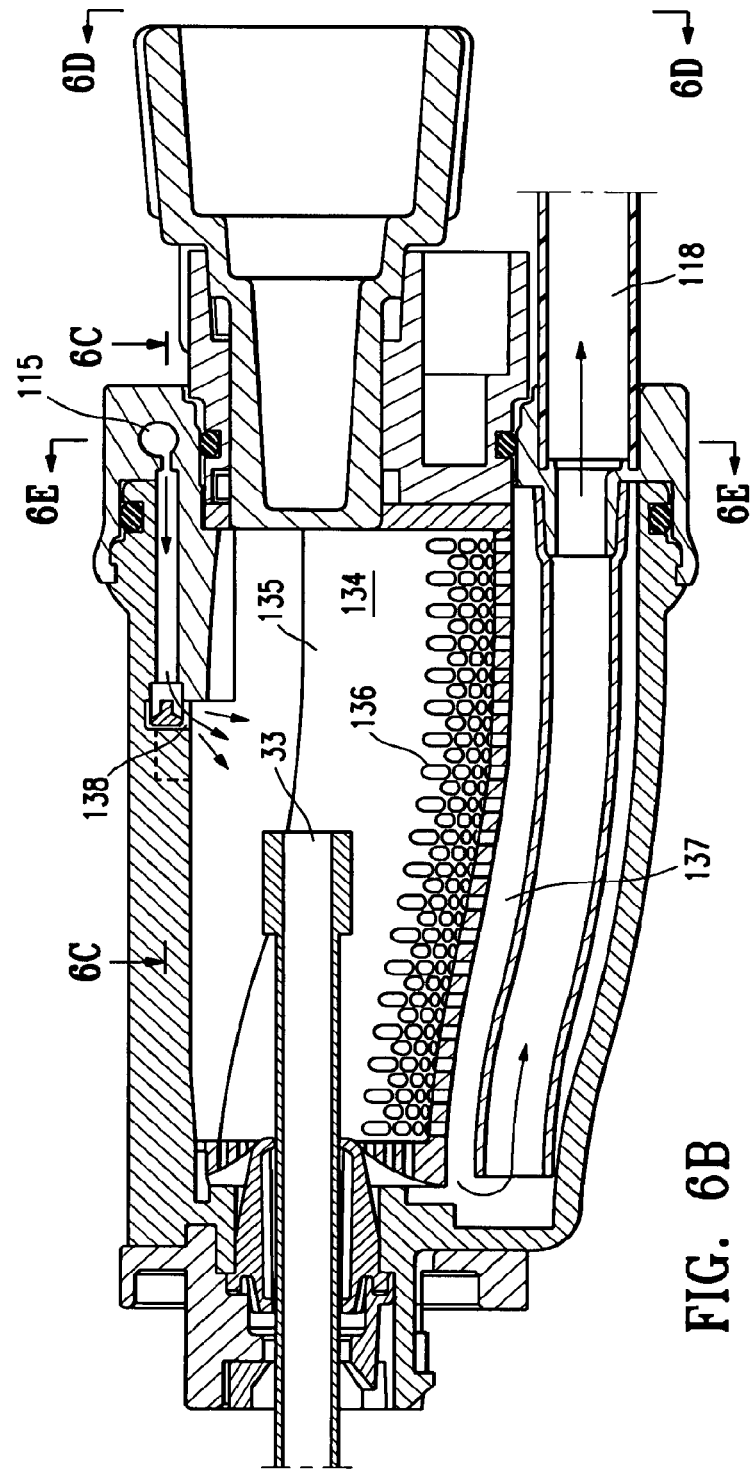

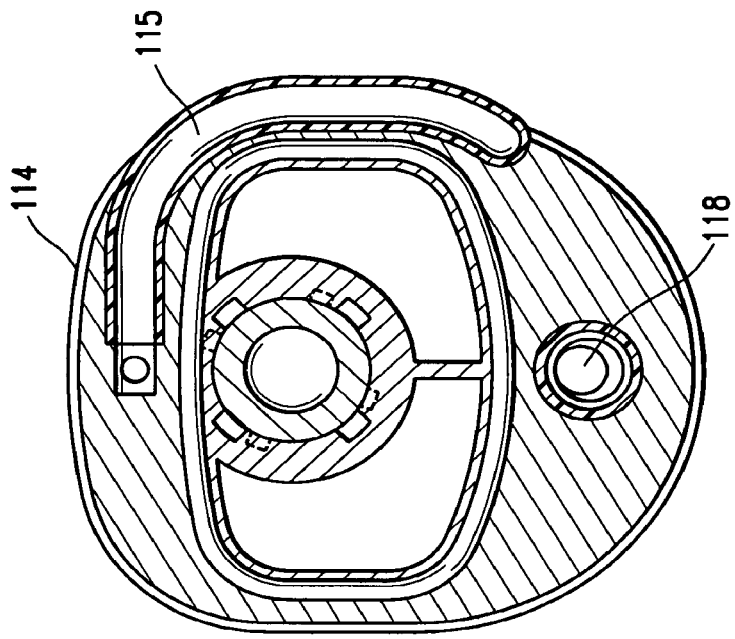
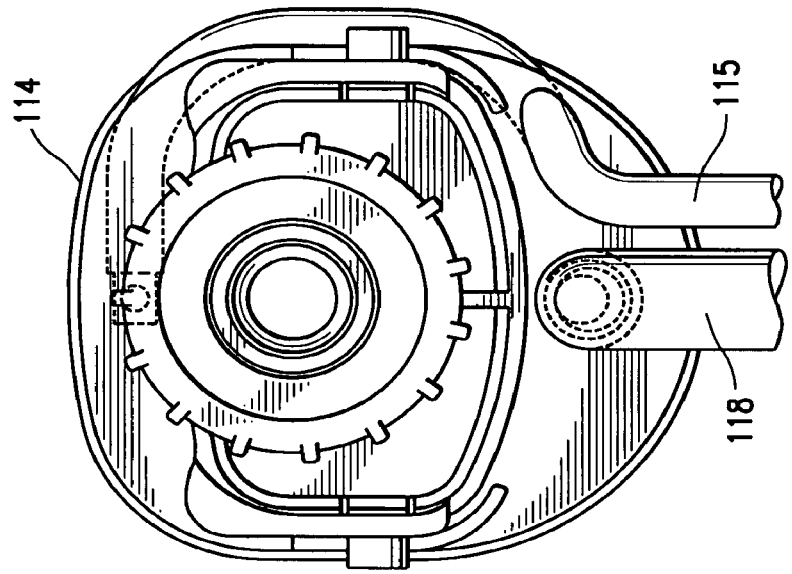
FIG. 6E
FIG. 6D

BIOPSY DEVICE WITH FLUID DELIVERY TO TISSUE SPECIMENS

RELATED APPLICATIONS

This application is a continuation of application Ser. No. 11/980,298, filed Oct. 30, 2007, now U.S. Pat. No. 8,317,725, which is a divisional of application Ser. No. 11/498,504, filed Aug, 3, 2006, now U.S. Pat. No. 7,572,236, which is a continuation-in-part of application Ser. No. 11/197,827 filed Aug. 5, 2005, now abandoned, each of which is incorporated herein in its entirety by reference.

FIELD OF THE INVENTION

The present invention relates generally to tissue removing devices such as biopsy devices and the methods of using such devices. More specifically, it is directed to an improved biopsy or other tissue removing device and method of using the device which includes flushing one or more specimens with suitable fluid within a tissue collector to remove blood, debris and the like from the specimen(s).

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

A variety of tissue collecting components have been proposed for biopsy devices but they have not always been easy for the physician or other operating room personnel to separate or remove the specimen from the device. Needle like tip designs have been developed to aid in the accessing of intracorporeal sites for biopsy and other procedures.

SUMMARY OF THE INVENTION

This invention is directed to a system and method for collecting one or more severed tissue specimens from a target site which includes the application of a fluid such as saline to one or more collected tissue specimens. The fluid may be applied to the one or more tissue specimens to flush blood and other debris from the one or more collected tissue specimens and/or to apply one or more agents to the collected tissue specimens. The tissue specimens are preferably collected within a tissue collector associated with a biopsy system. The fluid is preferably applied to at least one tissue specimen after it has been collected within the tissue collector but fluid may be applied as the tissue is delivered into the tissue collector. A vacuum may be generated within the tissue collector to remove the fluid from the specimens. The tissue collector component is preferably part of the biopsy system and easily removable therefrom so that the specimens may be removed without interfering with the position of the biopsy device.

A biopsy system having the tissue collection and fluid applying features of the invention generally include an elongated, preferably disposable probe component having an elongated tubular shaft, an elongated cutting member within the inner lumen of the elongated tubular shaft, a proximal housing that is secured to the proximal portion of the elongated tubular shaft and a tissue collector secured to the proximal housing in fluid communication with the inner lumen of the cutting member. The tissue cutter has a distal cutting edge to separate a tissue specimen from supporting tissue at an intracorporeal target site, an inner lumen to withdraw one or more tissue specimens and a proximal end with a discharge port which is configured to discharge specimens into the interior of the tissue collector.

A fluid delivery conduit extends from a source of fluid and opens to the interior of the tissue collector to deliver fluid to one or more specimens in the interior of the tissue collector. Preferably the fluid delivery conduit has a valve to control the fluid flow therethrough so as to sequence the flow of fluid to the interior of the tissue collector after the delivery of a tissue specimen. The fluid is preferably sprayed onto the specimens, for example by one or more spray heads or nozzles that may be provided. A controller may be provided to control the operation of the valve in the fluid delivery conduit to control fluid flow thereto.

A vacuum conduit may extend from a lower portion of the tissue collector to generate a vacuum within the interior of the tissue collector to aid in the aspiration of fluid and debris from the specimens. The vacuum within the tissue collector interior may also be employed to facilitate aspiration of one or more tissue specimens through the inner lumen of the tubular cutter. The vacuum conduit preferably leads to a waste container which captures the waste (fluid and debris) from the interior of the tissue collector. Preferably, a second vacuum conduit leads from the waste container to a vacuum source such as a vacuum pump which maintains a vacuum within the waste container. A controller may be utilized to control the operation of the vacuum pump to control the level of vacuum in the waste container and the interior of the tissue collector. The controller controlling the vacuum pump may be the same controller controlling the fluid control valve referred to above.

A suitable biopsy device which may be utilized with specimen flushing features of the invention is described in co-pending application Ser. No. 11/014,413, filed on Dec. 16, 2004. The housing on the proximal end of the probe has driving elements for the tissue cutter and other operative elements such as described in the aforesaid co-pending application which is incorporated herein by reference.

The elongated probe component preferably has a distal shaft portion with a tissue penetrating distal tip, a tubular section proximal to the distal tip, an inner lumen extending within the tubular section and an open, tissue receiving aperture in the tubular section proximal to the distal tip which provides access to tissue at the targeted site. The probe component includes an elongated tissue-cutting member, which is preferably at least in part cylindrically shaped and slidably disposed within the inner lumen of the tubular section. The tissue cutting member is provided with at least one tissue cutting edge on its distal portion which is configured to sever tissue extending into the interior of the tubular section through the aperture thereof. The cutting edge on the tissue cutting member may be configured for longitudinal cutting movement and may include oscillating rotational motion and/or reciprocating longitudinal motion to sever specimen tissue extending through the aperture from supporting tissue at the targeted site. The cutting edges are radially spaced from a longitudinal axis of the probe component and are preferably transversely oriented with respect to the longitudinal axis of the probe component. The tissue cutter is preferably slidably disposed within the inner lumen of the tubular section, although it may be disposed about the tubular section. The probe component may also have a handle which releasably engages a driver component as described in the above referenced application.

The tissue cutting member has an inner lumen preferably extending to a discharge port in the proximal end thereof for tissue specimen removal. While mechanical withdrawal of the tissue specimen may be employed, it is preferred to provide a vacuum within the cutting member from the proximal end of the cutting member (via the tissue collector interior) to aspirate the severed tissue specimen through the inner lumen of the cutting member to a tissue collection station. A higher fluid pressure may be maintained in the inner lumen of the cutting member distal to the tissue specimen to aid in transporting the specimen proximally through the inner lumen. In this manner, the mechanical withdrawal and/or the vacuum on the proximal end of the specimen and a higher pressure on the distal end of the specimen can move the specimen through the inner lumen of the cutting member to the tissue collector station.

In at least one embodiment described in the above mentioned application, the handle of the probe component is secured, preferably releasably secured, to the driver provided to interconnect the various operative elements of the probe with operative elements of the driver component. The tissue cutting member is operatively connected to at least one driver to provide the desired cutting motion. The proximal end of the tubular section of the probe component is fixed within the handle housing so that the orientation thereof with respect to the longitudinal axis and therefore the orientation of the tissue receiving aperture within the tubular section, can be selected by rotation of the handle housing with respect to the driver component. The orientation of the aperture may be selected manually such as described in copending application Ser. No. 10/642,406, filed Feb. Aug. 15, 2003 or it may be preset or selected electronically by a control module which also controls the operation of the cutting member and electrical power such as described in copending application Ser. No. 11/014,413, filed Dec. 16, 2004. The aperture orientation setting may be selected before or after the tubular section of the probe component is inserted into the patient.

A method of collecting one or more severed tissue specimens with a tissue collection device embodying features of the invention includes advancing a biopsy or other tissue removal system having such a tissue collecting device at least partially into tissue at a desired site within the patient's body with the tissue penetrating distal tip of the outer cannula disposed distal to the tissue specimen to be separated from the target site. A vacuum is established within the inner lumen of the tubular section to draw tissue through the aperture therein into the inner lumen of the tubular section. The cutting member, which is slidably disposed within the inner lumen of the tubular section, may then be moved, e.g. longitudinally, to cut a tissue specimen from supporting tissue at the target site by such cutter motion. The cutter motion preferably includes oscillating rotational movement and/or reciprocating longitudinal movement. The vacuum established within the inner lumen of the tubular section may be applied through the inner lumen of the tissue cutting member when the tissue cutting member is disposed within the tubular section. The applied vacuum within the inner lumen of the tissue cutting member from the vacuum of the tissue collector interior, may also be utilized to pull or aspirate the separated tissue sample proximally. In addition, or alternatively, a higher fluid pressure may be maintained in a distal part of the inner lumen of the tubular section, distal to the specimen, to push the tissue specimen proximally, Alternatively, the tissue specimen may be mechanically withdrawn. Fluid pressure may include pressure from a liquid delivered into the interior of the device, such as a physiological saline solution, and may include a gas, such as pressurized carbon dioxide, nitrogen or air, delivered into the interior of the device. Access to ambient air can also maintain a sufficiently high pressure differential to move the specimen through the inner lumen of the cutting member. Anesthetic may be injected to the target site through the outer cannula or the inner lumen of the cutting member.

The one or more tissue specimens are discharged into the interior of the tissue collector and preferably onto a tray provided therefore in the interior. The tray preferably has one or more openings which allow for drainage from the specimens on the tray. Irrigation (or other) fluid is applied to one or more specimens to remove blood or other debris. The periphery of the tissue collection tray is sealed within the interior of the tissue collector so that vacuum generated beneath the tray will aspirate fluid and debris from specimens on the tray to a vacuum conduit opening beneath the collector tray. The application of the irrigation fluid is preferably controlled to sequence after one or more tissue specimens are discharged onto the tissue collector tray from the discharge port in the proximal end of the tissue cutter. The fluid may contain or be a treating agent suitable for the subsequent evaluation of the specimens.

Upon removal from the patient, the tissue specimen may then be subjected to pathological examination. After acquisition of a tissue specimen or specimens, the tissue separation system may be repositioned for further tissue separation and collection or it may be withdrawn from the patient.

These and other advantages of the invention will become more apparent from the following detailed description of the invention and the accompanying exemplary drawings.

BRIEF DESCRIPTION OF THE DRAWINGS

FIG. 6A is a perspective view, with exterior portions partially in phantom, of a modified tissue collector.

FIG. 6B is a longitudinal cross sectional view taken along lines 6B-6B shown in FIG. 6A.

FIG. 6C is a transverse cross-sectional view of the tissue receiving tray shown in FIG. 6B taken along the lines 6C-6C.

FIG. 6D is an end view of the tissue collector shown in FIG. 6B taken along the lines 6D-6D.

FIG. 6E is a transverse cross-sectional view of the tissue collector shown in FIG. 6B taken along the lines 6E-6E.

DETAILED DESCRIPTION OF EMBODIMENTS OF THE INVENTION

Figure 1:
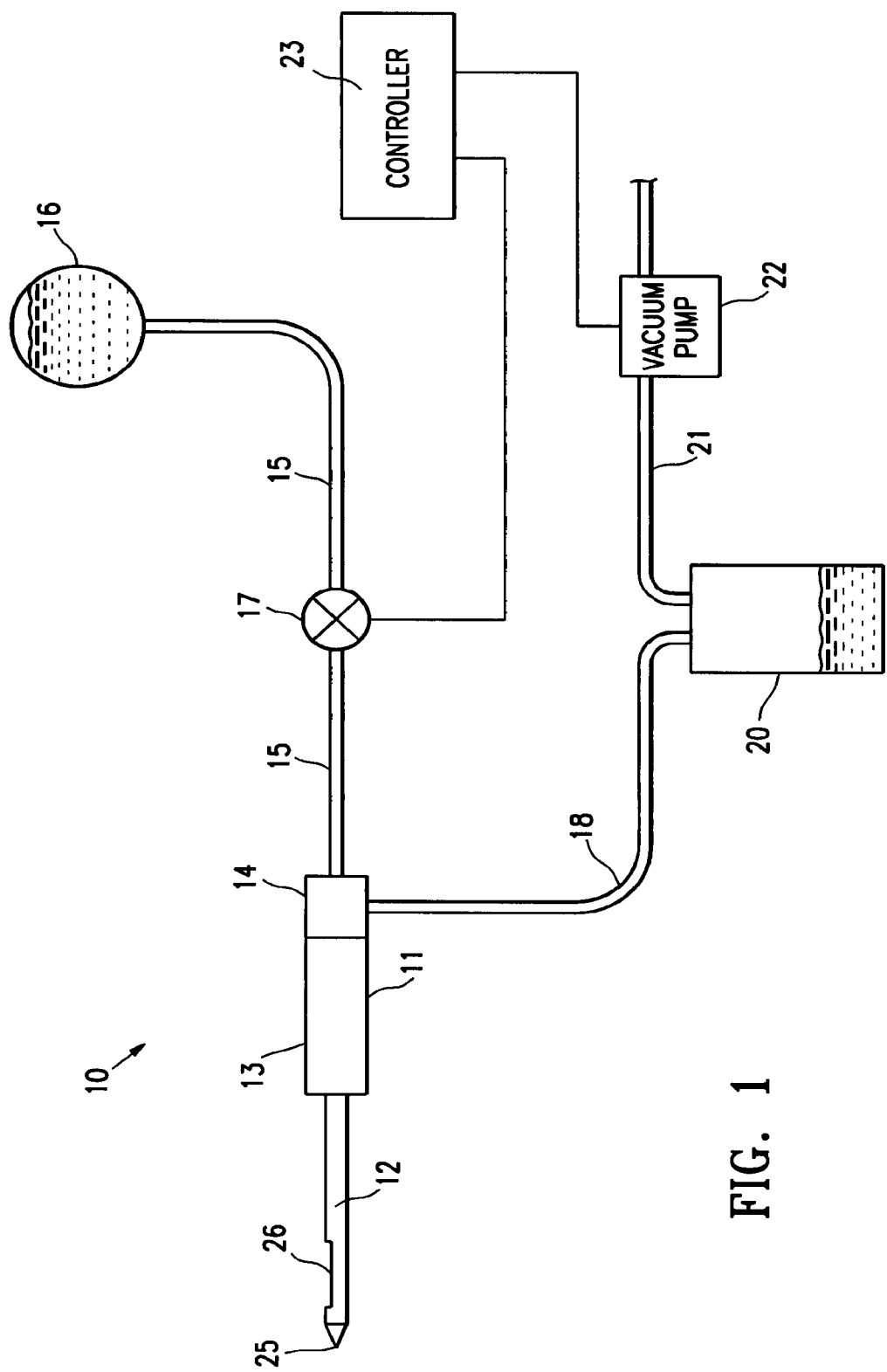
FIG. 1 is a schematic view of a biopsy system having a tissue specimen collector with flush and aspiration that embodies features of the invention.
Figure 2:
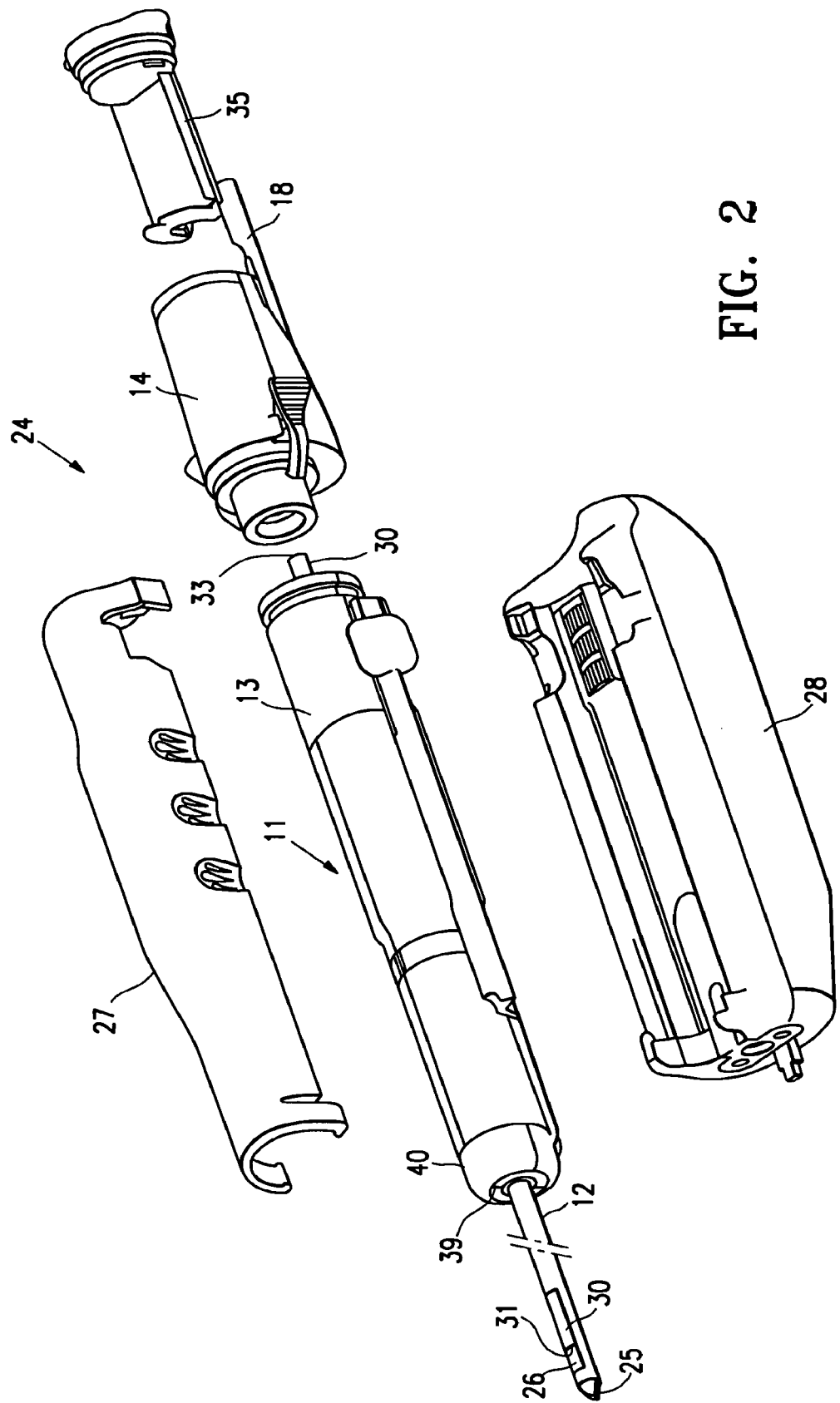
FIG. 2 is an exploded perspective view of the elongated tissue biopsy system shown in FIG. 1.
Figure 3:
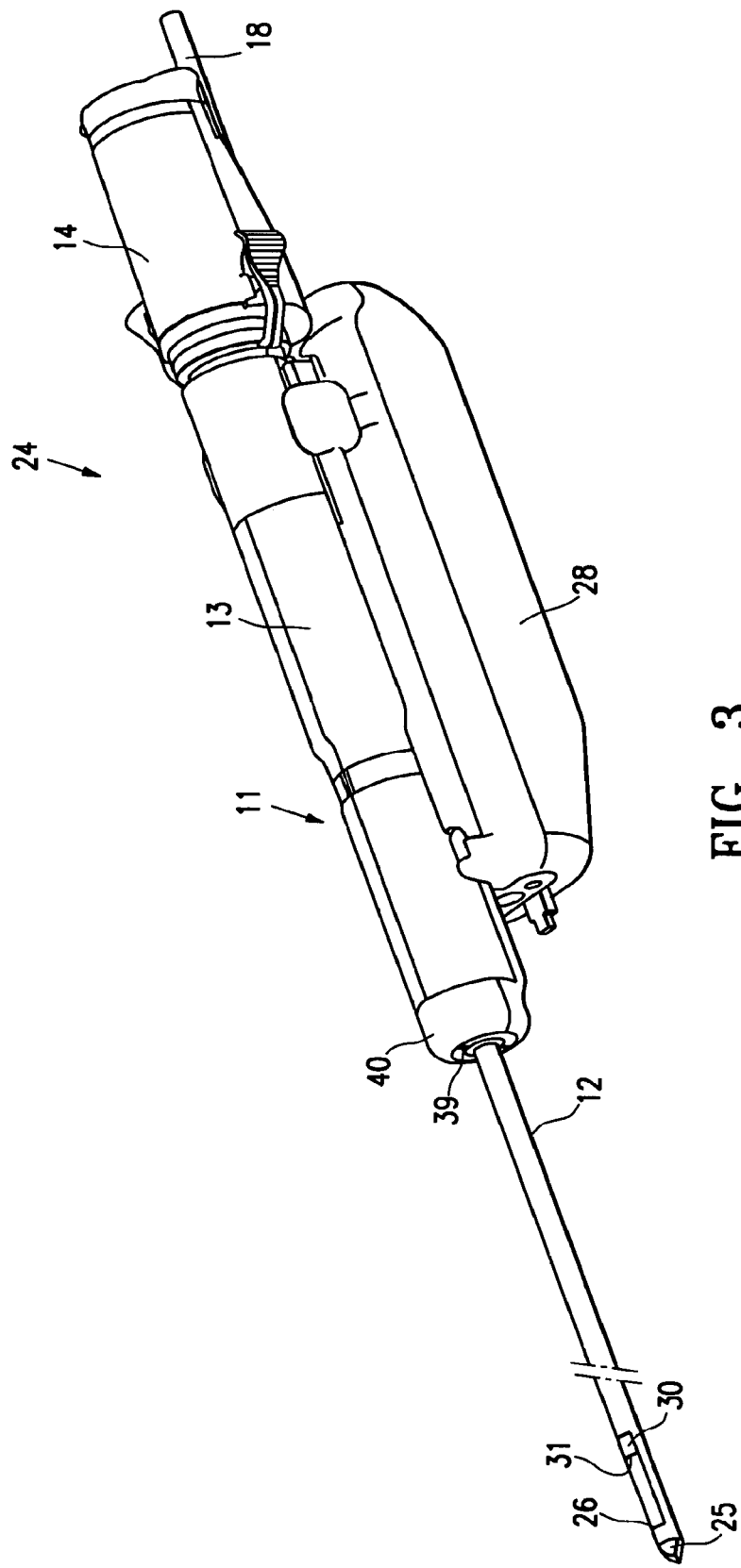
FIG. 3 is a perspective view of the embodiment shown in FIG. 2 in an assembled condition without a cover for the probe component.
Figure 4:
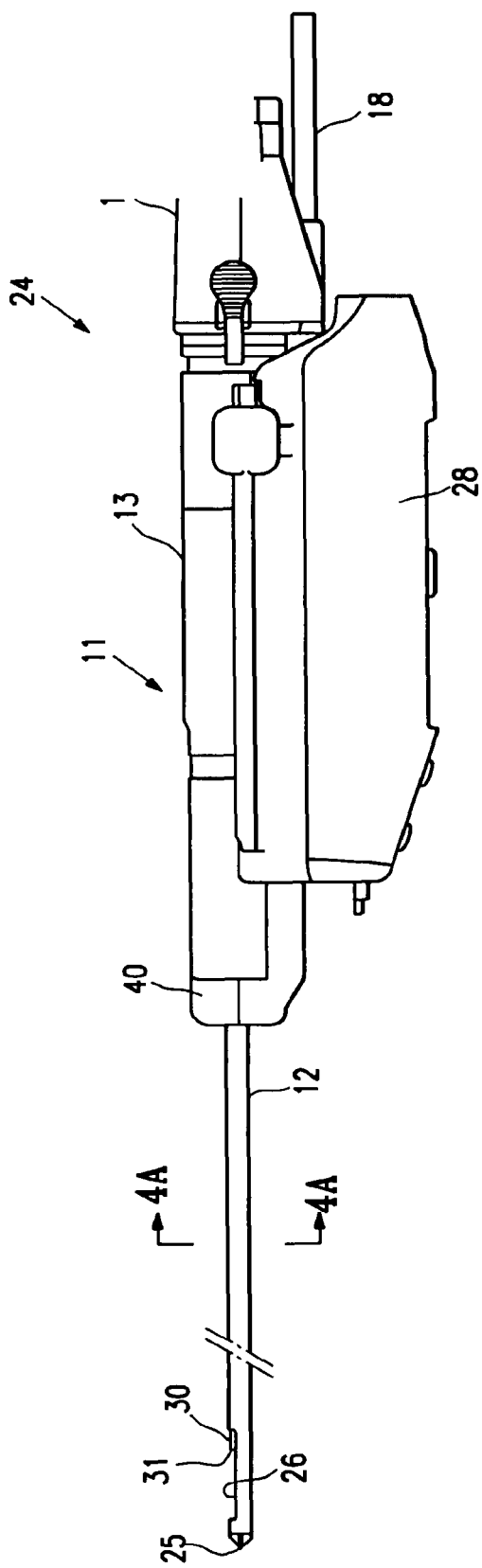
FIG. 4 is a side elevational view of the tissue biopsy system shown in FIG. 3.
Figure 4A:
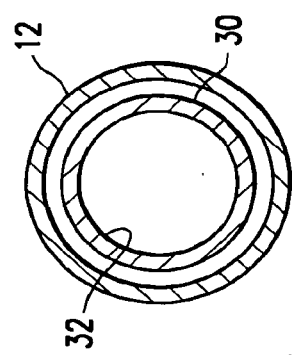
FIG. 4A is a transverse cross-sectional view of the probe component taken along the lines 4A-4A shown in FIG. 4
Figure 5A:
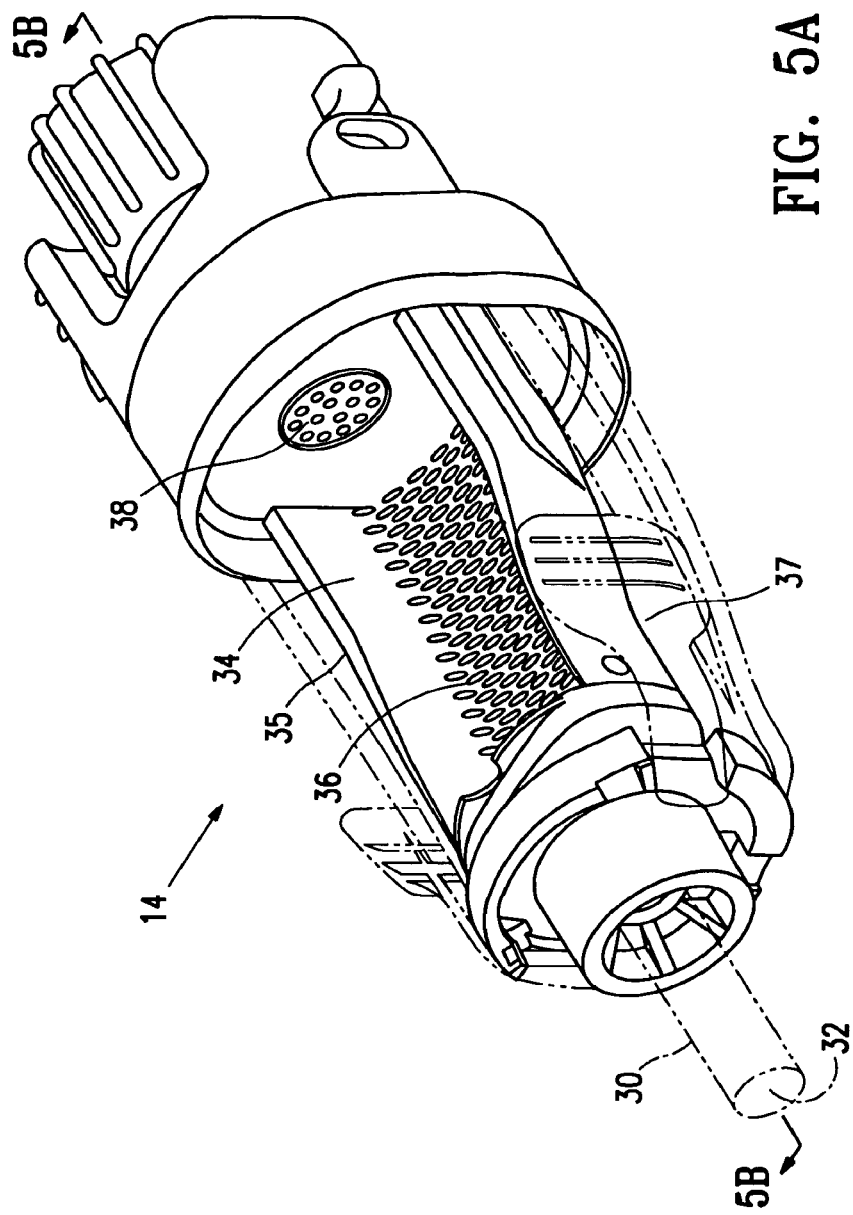
FIG. 5A is a perspective view, with exterior portions partially in phantom, of a tissue collector shown in FIG. 4.
Figure 5B:
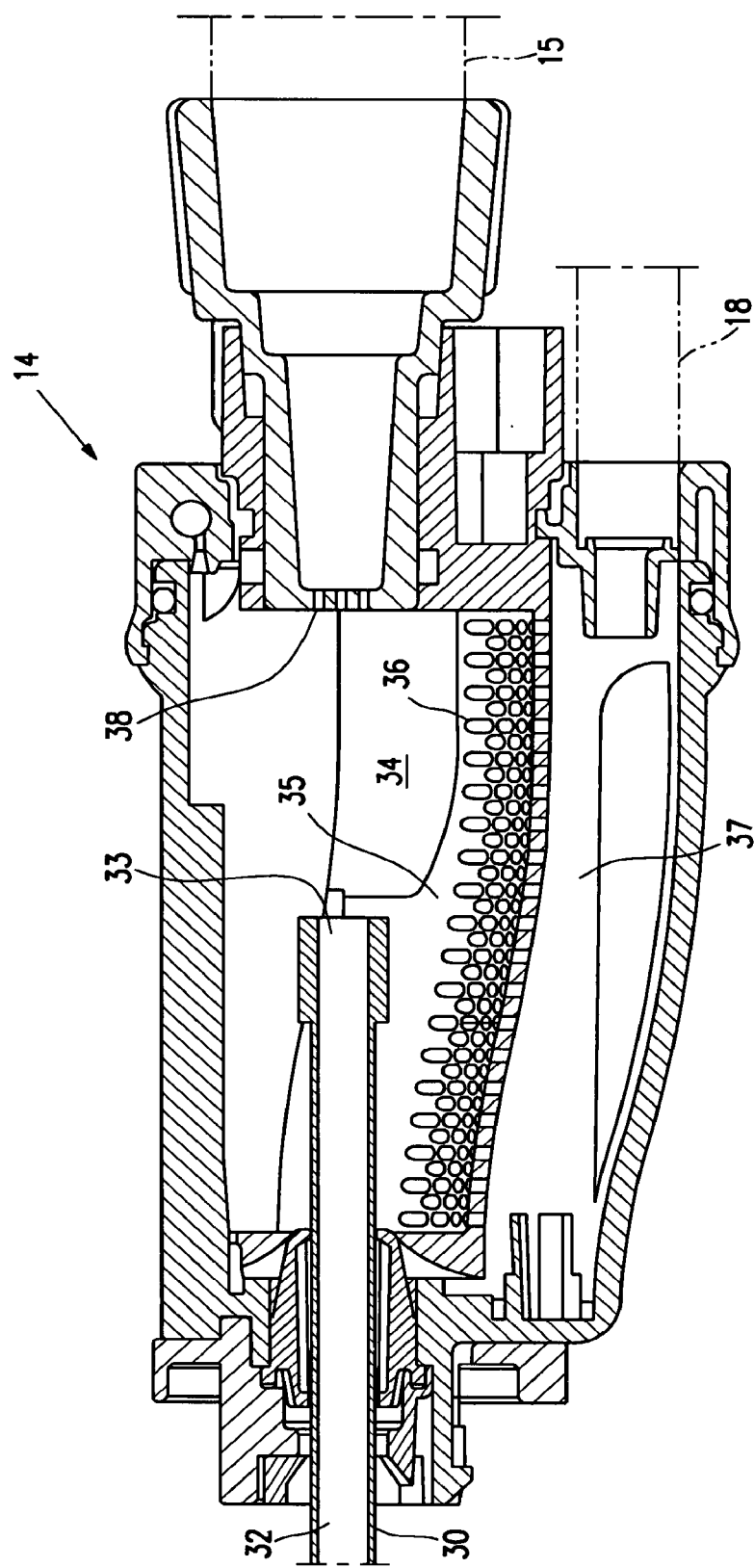
FIG. 5B is a longitudinal cross sectional view taken along lines 5B-5B shown in FIG. 5A.
Figure 5C:
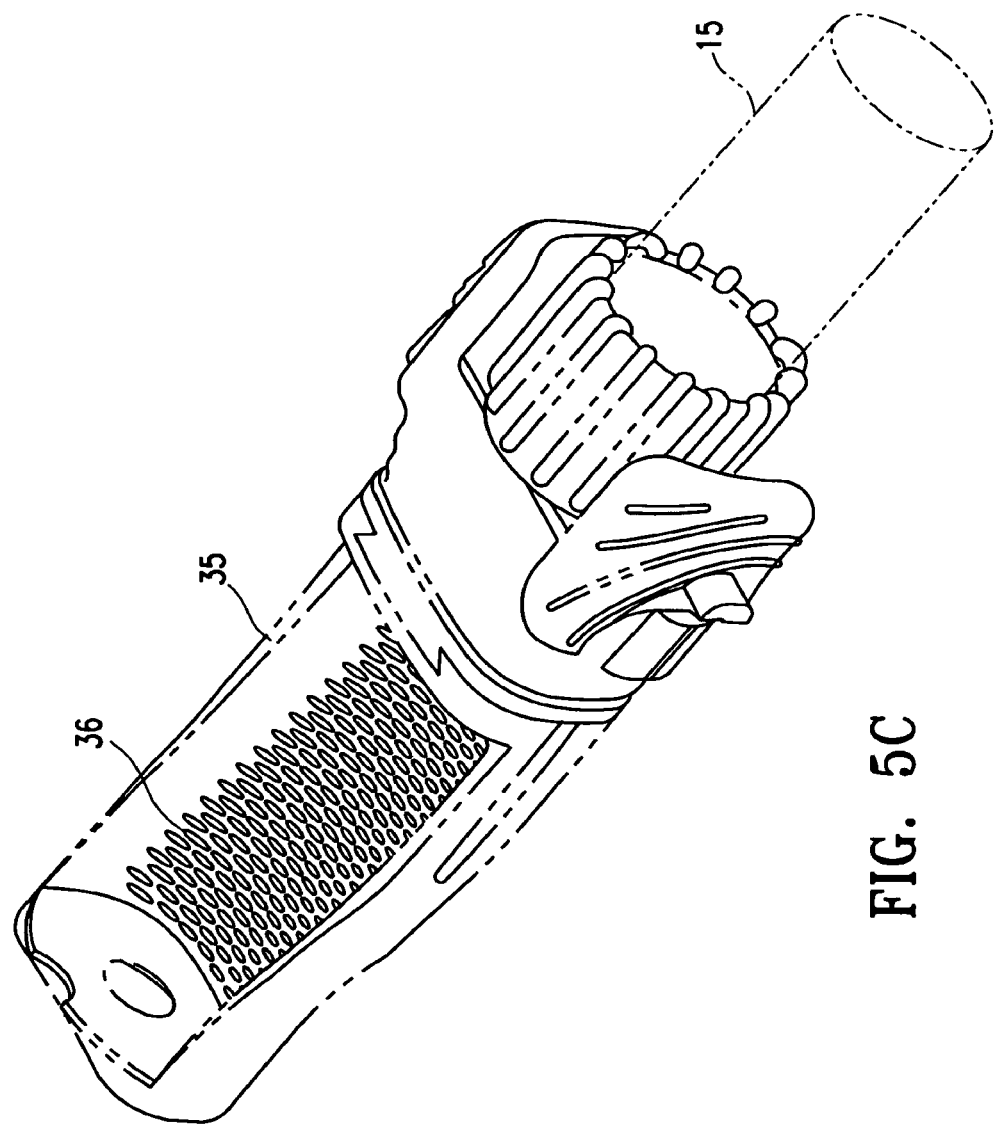
FIG. 5C is a perspective view of the tissue receiving tray shown in FIG. 5A.
Figure 5D:
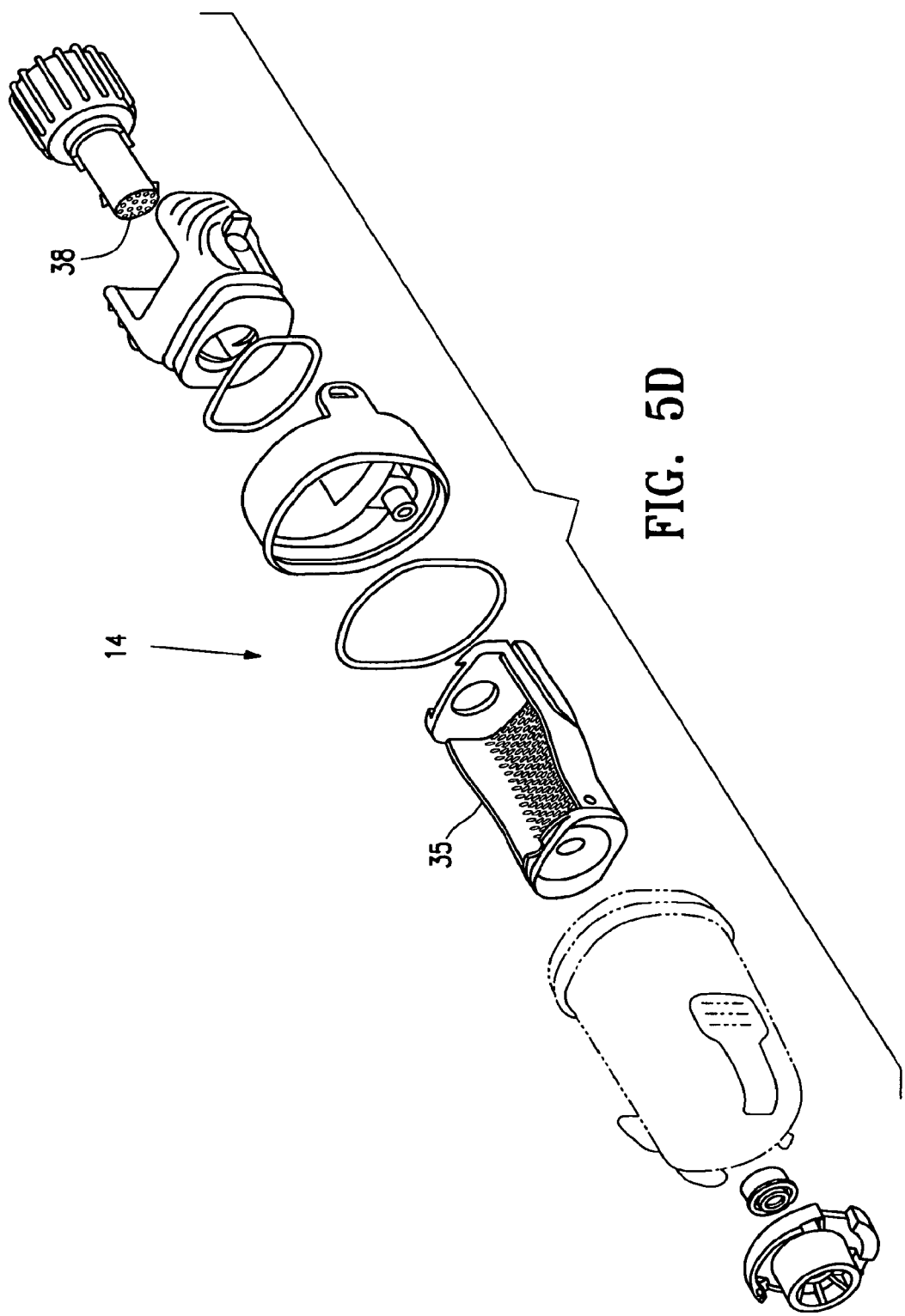
FIG. 5D is an exploded perspective view of tissue collector shown in FIG. 5A.
Figure 5E:
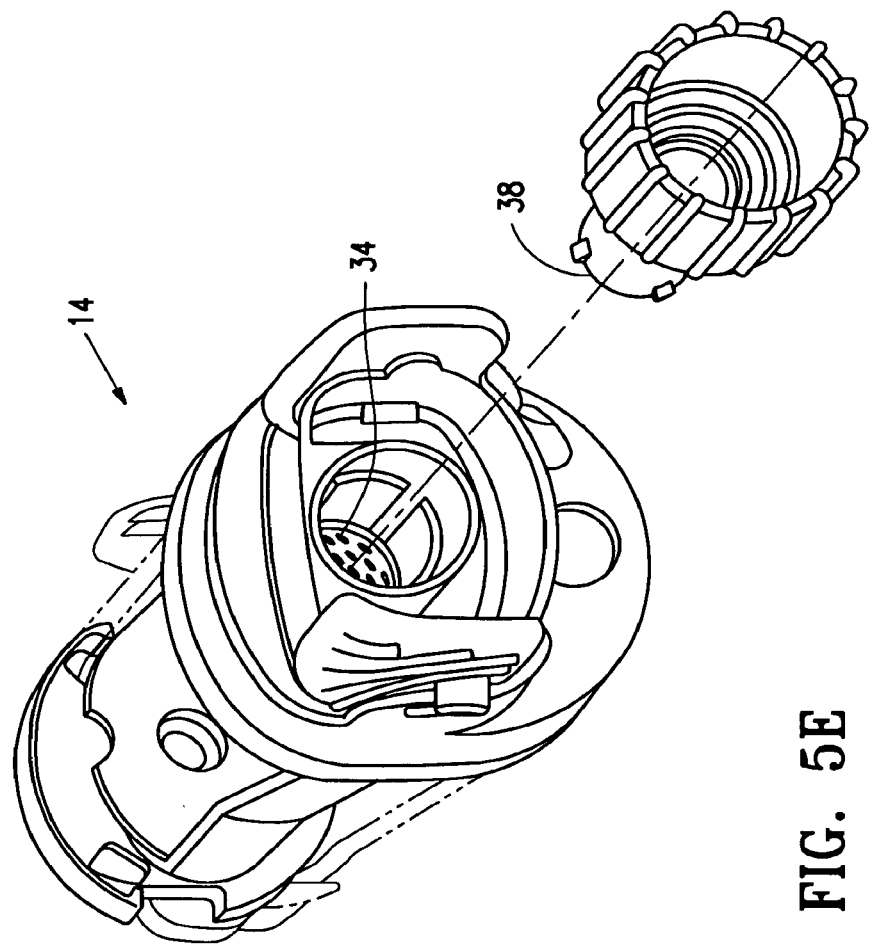
FIG. 5E is an end view in perspective of the tissue collector shown in FIG. 5A.
Figure 6F:
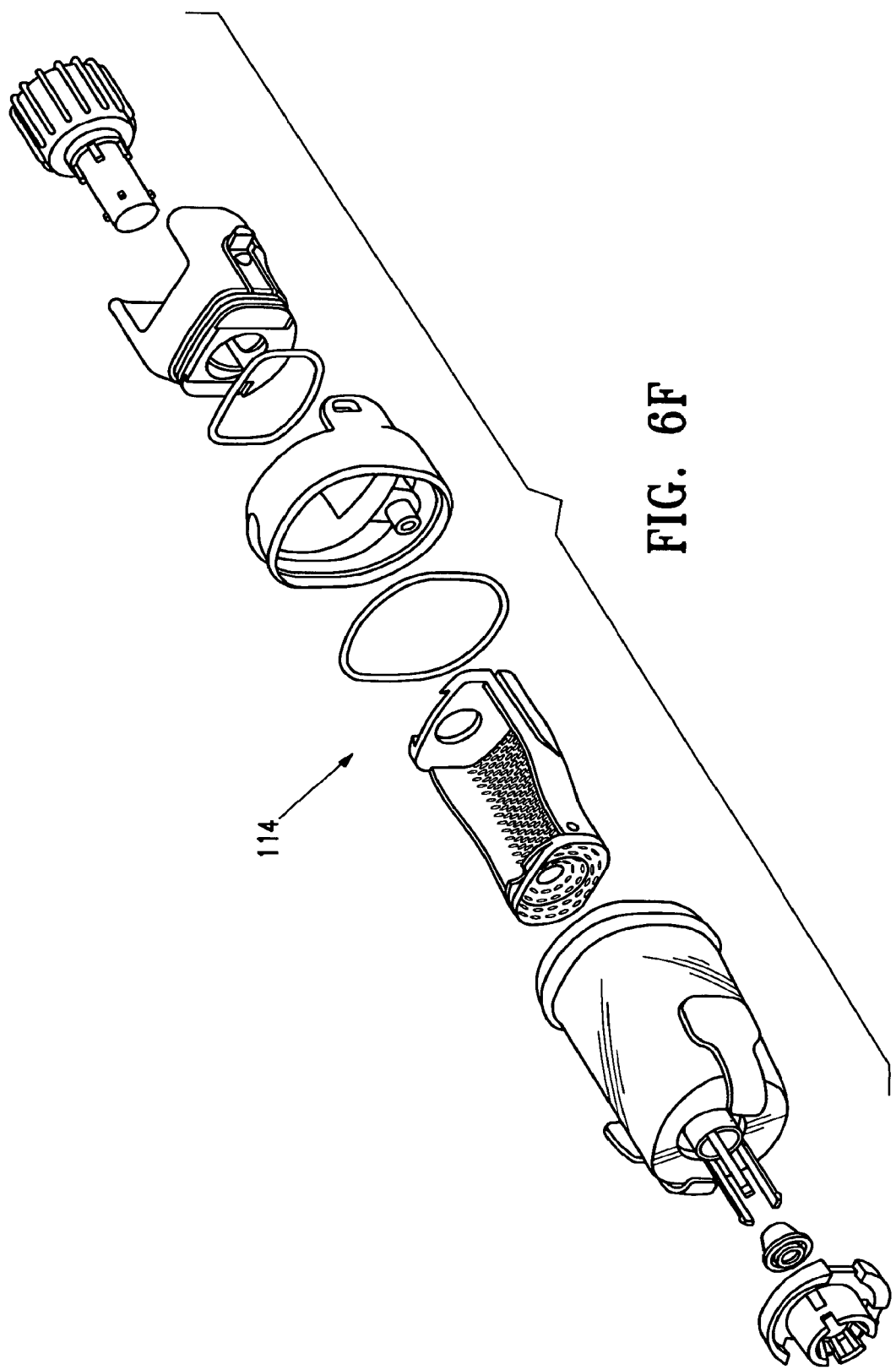
FIG. 6F is an exploded perspective view of tissue collector shown in FIG. 6A.
Figure 6G:
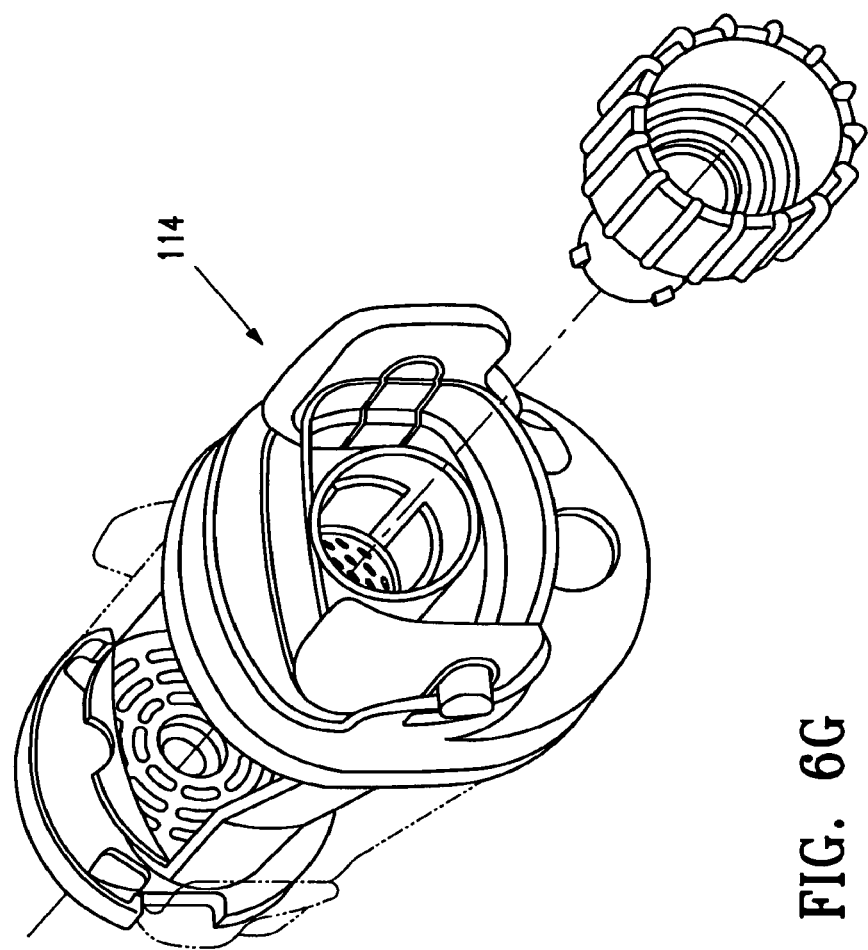
FIG. 6G is an end view in perspective of the tissue collector shown in FIG. 6A.

FIG. 1 schematically illustrates a biopsy system 10 embodying features of the invention. The system 10 includes a probe component 11 with an elongated tubular section 12, a proximal housing 13 and a tissue specimen collector 14 attached to the proximal housing. A first conduit 15 extends from fluid source 16 to the proximal end of the tissue collector 14 to deliver fluid to tissue specimens in the interior of the collector. A valve 17 is provided to control the fluid flow through the first conduit 15. A second conduit 18 extends to the tissue specimen collector 14 for application of a vacuum to the interior of the tissue specimen collector to aspirate fluid applied to one or more severed tissue specimens within the specimen collector. The second conduit 18 directs the aspirated fluid and debris to waste container 20. A third conduit 21 extends from the waste container 20 to a vacuum pump 22 which provides vacuum to the waste container and ultimately to the interior of the tissue specimen collector 14. The operation of the valve 17 in the fluid delivery conduit 15 and the vacuum pump 22 connected to the third conduit 21 may be controlled by controller 23.

FIGS. 2-5A-E illustrate the biopsy device 24 of the system 10 in further detail. The probe component 11 generally includes an elongated tubular section or cannula 12 with a tissue penetrating tip 25 on the distal end thereof and an open, tissue receiving aperture 26 proximally adjacent to the distal tip. The probe component 11 also includes a proximal housing 13 which contains the driving mechanisms for the various elements of the probe component. Probe housing cover 27 is configured to interfit with the driver component 28 so as to enclose the proximal housing 13 of the probe component 11. A tissue cutter 30 is slidably disposed within the probe component 11 and has a distal cutting edge 31 which severs tissue that extends through the tissue receiving aperture 26. An inner lumen 32 extends through the tissue cutter 30 to the tissue discharge port 33 in a proximal portion of the tissue cutter which discharges tissue specimen into the interior 34 of the tissue collector 14. The tissue discharge port 33 is preferably located at the proximal end of the tissue cutter 30.

The details of driver component 28 and the interaction between the driver component and the probe component 11 can be found in the above mentioned application Ser. No. 11/014,413.

The tissue specimen collector 14 (shown in more detail in FIGS. 5A-5E) is secured to the proximal end of the housing 13 of probe component 11 and has an interior 34 in fluid communication with the inner lumen 32 of the tissue cutter 30 through tissue discharge port 33. The interior 34 of the specimen collector 14 has a specimen receiving basket or tray 35, preferably removable, which is configured to receive tissue specimens from the discharge port 33 which may have been drawn therein. The tray 35 may have a grated portion 36 (or foraminous or is otherwise provided with a plurality of openings) to provide fluid communication with the vacuum chamber 37 provided under the tray. A vacuum is generated within the interior 34 by the vacuum within the vacuum chamber 37 to draw tissue specimens through the inner lumen 32 of the cutter 30 into the interior 34 of the tissue collector 14. The first vacuum conduit 18 has a distal end which is in fluid communication with the vacuum chamber 36 and has a proximal end which is configured to be connected to a waste container 20. Alternatively, the first vacuum conduit 15 may be directly connected to a vacuum source such as vacuum pump 22.

Application of a vacuum within the tubular section 12 aids in pulling tissue into the interior thereof through the tissue receiving aperture 26 and the transfer of the severed tissue specimen through the inner lumen 32 of the tissue cutter 30 and the deployment of the specimen onto the collection tray 35 within the tissue collector 14. Preferably, the vacuum is applied under the tray 35 in vacuum chamber 37 to facilitate removal of fluid and/or debris from the one or more specimens that may be on the upper surface of tray 35.

Fluid delivery conduit 15 has a spray head 38 which discharges into the interior 34 over the tray 35 so as to spray fluid onto one or more specimens located on the tray. The low pressures in the vacuum chamber 37 under the tray 35 aspirates fluid and debris through the openings of grated portion 36 of the tray. Fluids include blood from the specimen and fluids injected or sprayed into the chamber 34 of the tissue collector 14 through the spray head 38. The size of the debris aspirated into the vacuum chamber is limited for the most part by the size of the openings in grated portion 36. Preferably, the delivery of flushing fluid to the chamber 34 is controlled to sequence after aspiration of one or more tissue specimens onto the tray 35. Saline is a suitable fluid, but other fluids may be used. A variety of agents, such as thrombolytic agents, e.g heparin, may be incorporated into the fluid to break up thrombus which may have formed on the specimen. Treatment fluids may also be employed for the subsequent examination of the one or more specimens.

The tissue penetrating distal tip 25 may have a variety of tip shapes. Particularly suitable distal tips are disclosed in the above mentioned co-pending application Ser. No. 11/014,413.

In use, the distal end of the probe component 11 is advanced within the patient with the tissue cutter 30 in a forward position to close off the tissue receiving aperture 26 of the tubular section 12 until the aperture is located in a desired location within the patient for taking a tissue specimen. The tissue cutter 30 is then withdrawn proximally to an open position to open up the aperture 26. The withdrawal of the tissue cutter 30 can be used to control the length of the aperture which is opened in order to control the length of the specimen which is drawn into the interior of the tubular section 12 and severed from supporting tissue. A vacuum is applied to the inner lumen 32 of the tissue cutter 30 through the interior 34 of the tissue collector 14 to draw tissue at the site into the inner lumen of the tubular section 12 through the aperture 26. The tissue cutter 30 is then driven distally and rotated or oscillated to sever the aspirated tissue specimen from the supporting tissue at the target site with the tissue cutting edge 31. The vacuum within the inner lumen 32 of the tissue cutter 30 aids or causes the severed tissue specimen to be drawn through the inner lumen of the tissue cutter and into the interior 34 of specimen collector 14. Positive pressure or even ambient conditions distal to the tissue specimen in the lumen 32 can help tissue specimen passage through the inner lumen to the discharge port 33 of the tissue cutter 30. If another tissue specimen is desired, the tubular section 12 may be rotated in one or more steps to move the aperture 26 to another location and repeat obtaining another tissue specimen in the same manner without otherwise moving the biopsy device 24. Typically, tissue specimens are obtained sequentially with the aperture 26 of the probe 11 in the 12, 2, 4, 6, 8, 10 o-clock positions and then in the 1 3, 5, 7, 9 and 11 o-clock positions. Other sequences for obtaining tissue specimens may be employed. The position of the aperture 26 may be indicated by a marker arrow 39 at the distal end cap 40 (FIG. 2) of proximal housing 13 so that the physician or other operating personnel can readily determine what the orientation of the aperture 26 within the patient. The biopsy system 10 may be hand held for some biopsy procedures or the system may be mounted on a stereotactic mounting stage such as a shoe that is slidably mounted to a rail of a Fischer or Lorad stage as discussed in the above mentioned application Ser. No. 11/014,413.

Fluid from a source 16 may be delivered through first conduit 15 to the interior 34 of tissue collector 14 and sprayed onto the one or more specimens on the grated portion of the tray 35. Vacuum generated in the vacuum chamber 36 under the tray 35 aspirates fluid and small dimensioned debris through the grated openings of the tray into the vacuum chamber 37. Fluid and debris are aspirated from vacuum chamber 36 through second conduit 18 into the waste container 20. Third conduit 21 maintains vacuum conditions in the interior of waste container 20 by the vacuum pump 22.

An alternative tissue specimen collector 114 is shown in detail in FIGS. 6A-6G) which is secured to the proximal end of the housing 13 of probe component 11 and has an interior 134 in fluid communication with the inner lumen 32 of the tissue cutter 30 through tissue discharge port 33. The interior 134 of the specimen collector 114 has a specimen receiving basket or tray 135, preferably removable, which is configured to receive tissue specimens from the discharge port 33 which may have been drawn therein. The tray 135 has a grated portion 136 (or foraminous or is otherwise provided with a plurality of openings) to provide fluid communication with the vacuum chamber 137 provided under the tray. A vacuum is generated within the interior 134 by the vacuum within the vacuum chamber 137 to draw tissue specimens through the inner lumen 32 of the cutter 30 into the interior 134 of the tissue collector 114. The vacuum conduit 118 has a distal end which is in fluid communication with the vacuum chamber 137 and has a proximal end which is configured to be connected to a waste container 20. Alternatively, the vacuum conduit 115 may be directly connected to a vacuum source such as vacuum pump 22 as shown in FIG. 1.

Fluid delivery conduit 115 has a spray head 138 which discharges into the interior 134 over the tray 135 so as to spray fluid onto one or more specimens located on the tray. The low pressures in the vacuum chamber 137 under the tray 135 aspirates fluid and debris through the openings of grated portion 136 of the tray. Fluids include blood from the specimen and fluids injected or sprayed into the chamber 134 of the tissue collector 114 through the spray head 138, shown in detail in FIGS. 6B and 6C. The size of the debris aspirated into the vacuum chamber is limited for the most part by the size of the openings in grated portion 136. Preferably, the delivery of flushing fluid to the chamber 134 is controlled to sequence after aspiration of one or more tissue specimens onto the tray 135.

While particular forms of the invention have been illustrated and described herein, it will be apparent that various modifications and improvements can be made to the invention. For example, while the various embodiments of the invention have been described herein in terms of a biopsy device, it should be apparent that the tissue collector may be employed to remove tissue for purposes other than for biopsy, i.e. for treatment or other diagnoses. Alternatively, the tissue cutting element may be on the exterior of the probe device and the tubular component having the tissue receiving opening in the distal end may be disposed within the tissue cutting element. In the latter alternative embodiment, the tissue specimen may be transported through the tuular component having the tissue receiving opening.

Individual features of embodiments having features of the invention may be shown in some drawings and not in others, but those skilled in the art will recognize that individual features of one embodiment can be combined with any or all the features of another embodiment. Accordingly, it is not intended that the invention be limited to the specific embodiments illustrated.

Terms such a "element", "member", "device", "section", "component", "portion", "means", "step" and words of similar import, when used in the following claims, shall not be construed as invoking the provisions of 35 U.S.C. §112(6) unless the claims expressly use the term "means" followed by a particular function without specific structure or the term "step" or "steps" followed by a particular function without specific action.

All patents and patent applications referred to herein are incorporated by reference in their entirety.

What is claimed is:

1. A system for collecting one or more tissue specimens from a target site within a patient, comprising:
    an elongated probe component including:
        a distal shaft portion with a distal tip, a tubular section proximal to the distal tip, an inner lumen extending within the tubular section and a tissue receiving aperture in the tubular section which provides access to tissue at the target site, and
        an elongated tissue cutting member which has at least one tissue cutting edge;
    a collector housing defining an interior, and having a proximal opening and a distal port opposite the proximal opening, the distal port of the collector housing being configured to receive a proximal end of the elongated probe component such that the proximal end of the elongated probe component can extend into the interior of the collector housing; and
    a releasable tray that is releasably attached to the collector housing at the proximal opening, the releasable tray including:
        a first end portion; and
        a grated portion that extends from the first end portion, the grated portion being configured to extend through the proximal opening of the collector housing in a direction toward the distal port and into the interior to separate the collector housing to define a tissue chamber and a vacuum chamber, and configured such that a tissue discharge port of the elongated probe component is positioned in the tissue chamber above the grated portion, the grated portion having a plurality of holes to facilitate fluid communication between the tissue chamber and the vacuum chamber.

2. A tissue specimen collector for engagement with a proximal housing of a biopsy probe along a longitudinal extent of a tubular elongated member of the biopsy probe configured to transport a tissue sample, comprising:
    a collector housing defining an interior, and having a proximal opening and a distal port opposite the proximal opening, the distal port of the collector housing being configured to receive a proximal end of the tubular elongated member of the biopsy probe such that the proximal end of the tubular elongated member can extend into the interior of the collector housing; and
    a releasable tray that is releasably attached to the collector housing at the proximal opening, the releasable tray including:

a first end portion; and a grated portion that extends from the first end portion, the grated portion being configured to extend through the proximal opening of the collector housing in a direction toward the distal port and into the interior to separate the collector housing to define a tissue chamber and a vacuum chamber, such that a portion of the tubular elongated member is positioned in the tissue chamber above the grated portion, the grated portion having a plurality of holes to facilitate fluid communication between the tissue chamber and the vacuum chamber.

3. The tissue specimen collector of claim 2, wherein at least one of the collector housing and the releasable tray comprises a washing port extending to the interior of the collector housing, the washing port being in direct fluid communication with the tissue chamber, and the washing port being configured for fluid communication with a washing fluid source.

4. The tissue specimen collector of claim 3, wherein the washing port includes a spray head coupled to a fluid conduit, the spray head being located over the grated portion.

5. The tissue specimen collector of claim 3, wherein at least one of the collector housing and the releasable tray comprises a vacuum port extending to the interior of the collector housing, the vacuum port being in direct fluid communication with the vacuum chamber with the grated portion being interposed between the washing port and the vacuum port, the vacuum port being configured for fluid communication with a vacuum source.

6. The tissue specimen collector of claim 2, wherein the releasable tray having the grated portion is configured to be removably received in the interior of the collector housing along the longitudinal extent of the tubular elongated member.

7. The tissue specimen collector of claim 2, wherein the tubular elongated member is an elongated tissue cutting member.

8. The tissue specimen collector of claim 2, wherein the grated portion extends longitudinally from the first end portion, and further comprising a washing port and a vacuum port with the grated portion being interposed between the washing port and the vacuum port.

9. An elongated probe component for use in a system for collecting one or more tissue specimens from a target site within a patient, the system including a washing fluid source and a vacuum source, the elongated probe component comprising:

a tubular elongated member having a distal end and a proximal end, the distal end having at least one tissue cutting edge and the proximal end defining a tissue discharge port;

a proximal housing coupled to a proximal part of the elongated shaft; and a tissue specimen collector configured for engagement with the proximal housing along a longitudinal extent of the elongated tissue cutting member, the tissue specimen collector being secured to the proximal housing, the tissue specimen collector including:

a collector housing defining an interior, and having a proximal opening and a distal port opposite the proximal opening, the distal port of the collector housing being configured to receive a proximal end of the tubular elongated member of the biopsy probe such that the proximal end of the tubular elongated member can extend into the interior of the collector housing; and a releasable tray is releasably attached to the collector housing at the proximal opening, the releasable tray including:

a first end portion; and a grated portion that extends from the first end portion, the grated portion being configured to extend through the proximal opening of the collector housing in a direction toward the distal port and into the interior to separate the collector housing to define a tissue chamber and a vacuum chamber, and configured such that a tissue discharge port of the tubular elongated member is positioned in the tissue chamber above the grated portion, the grated portion having a plurality of holes to facilitate fluid communication between the tissue chamber and the vacuum chamber.

10. The elongated probe component of claim 9, wherein at least one of the collector housing and the releasable tray comprises a washing port extending to the interior of the collector housing, the washing port being in direct fluid communication with the tissue chamber, and the washing port being configured for fluid communication with the washing fluid source.

11. The elongated probe component of claim 10, wherein the washing port includes a spray head coupled to a fluid conduit, the spray head being located over the grated portion.

12. The elongated probe component of claim 10, wherein at least one of the collector housing and the releasable tray comprises a vacuum port extending to the interior of the collector housing, the vacuum port being in direct fluid communication with the vacuum chamber with the grated portion being interposed between the washing port and the vacuum port, the vacuum port being configured for fluid communication with the vacuum source.

13. The elongated probe component of claim 9, wherein the releasable tray having the grated portion is configured to be removably received in the interior of the collector housing along the longitudinal extent of the tubular elongated member with the tissue discharge port of the tubular elongated member extending over the grated portion.

14. The elongated probe component of claim 9, wherein the releasable tray having the grated portion is configured to be removably received in the interior of the collector housing along the longitudinal extent of the tubular elongated member.

15. The elongated probe component of claim 9, wherein the tubular elongated member is an elongated tissue cutting member.

16. The elongated probe component of claim 9, wherein the grated portion extends longitudinally from the first end portion, and further comprising a washing port and a vacuum port with the grated portion being interposed between the washing port and the vacuum port.

17. A tissue specimen collector for engagement with a proximal housing of a biopsy probe along a longitudinal extent of a tubular elongated member of the biopsy probe configured to transport a tissue sample, comprising:

a collector housing defining an interior, and having a proximal opening and a distal port opposite the proximal opening, the distal port of the collector housing being configured to receive a proximal end of the tubular elongated member of the biopsy probe such that the proximal end of the tubular elongated member can extend into the interior of the collector housing; and a releasable tray that is releasably attached to the collector housing at the proximal opening, the releasable tray including:

a first end portion; and a grated portion that extends from the first end portion, the grated portion being configured to extend through the proximal opening of the collector housing in a direction toward the distal port and into the interior to separate the collector housing to define a tissue chamber and a vacuum chamber, such that a tissue discharge port of the tubular elongated member is positioned in the tissue chamber above the grated portion, the grated portion having a plurality of holes to facilitate fluid communication between the tissue chamber and the vacuum chamber, and wherein the collector housing comprises a washing port extending to the interior of the collector housing, the washing port being in direct fluid communication with the tissue chamber, and the washing port being configured for fluid communication with a washing fluid source.

18. The tissue specimen collector of claim 17, wherein the collector housing comprises a vacuum port extending to the interior of the collector housing, the vacuum port being in direct fluid communication with the vacuum chamber with the grated portion being interposed between the washing port and the vacuum port, the vacuum port being configured for fluid communication with a vacuum source.

19. The tissue specimen collector of claim 17, wherein the grated portion extends longitudinally from the first end portion, and further comprising a washing port and a vacuum port with the grated portion being interposed between the washing port and the vacuum port.

* * * * *